United States Patent
Mantelmacher

(10) Patent No.: US 8,075,631 B2
(45) Date of Patent: Dec. 13, 2011

(54) PROSTHETIC SOCKET ADJUSTABLE TEST MOUNTING SYSTEM

(76) Inventor: H Lee Mantelmacher, Owings Mills, MD (US)

( * ) Notice: Subject to any disclaimer, the term of this patent is extended or adjusted under 35 U.S.C. 154(b) by 71 days.

(21) Appl. No.: 12/658,259

(22) Filed: Feb. 4, 2010

(65) Prior Publication Data
US 2010/0211188 A1    Aug. 19, 2010

Related U.S. Application Data

(60) Provisional application No. 61/206,893, filed on Feb. 5, 2009.

(51) Int. Cl.
*A61F 2/80* (2006.01)
(52) U.S. Cl. .......................................................... 623/33
(58) Field of Classification Search .............. 623/33–35, 623/38
See application file for complete search history.

(56) References Cited

U.S. PATENT DOCUMENTS

| | | |
|---|---|---|
| 5,047,063 A | 9/1991 | Chen |
| 5,163,965 A | 11/1992 | Rasmusson et al. |
| 5,545,230 A | 8/1996 | Kinsinger et al. |
| 5,545,231 A | 8/1996 | Houser |
| 6,051,026 A | 4/2000 | Biedermann |
| 6,123,732 A | 9/2000 | Gramnas |
| 6,458,163 B1 | 10/2002 | Slemker et al. |
| 6,669,736 B2 | 12/2003 | Slemker |

*Primary Examiner* — Bruce E Snow
(74) *Attorney, Agent, or Firm* — Ober, Kaler, Grimes & Shriver; Royal W. Craig

(57) ABSTRACT

A temporary diagnostic prosthetic socket mounting system and kit including a generally circular test mounting block defined by an annular groove and four axial cutouts extending from the lower surface of the block to the upper surface. The axial cutouts are at least as deep as the annular groove. A band extending around the perimeter of the block is provided which spans the axial cutouts, thereby forming a void in the cutouts beneath the tape. The block is secured to a prosthetic diagnostic socket by adhesive with the band extending up over the upper edge of the block and onto the outer surface of the socket. Casting tape is applied over the socket/block joint extending into the groove. After diagnostic fitting and transfer of the alignment, a cast saw can be passed around the joint through the casting tape and into the adhesive between the upper surface of the block and the rounded distal end of the socket. The gap behind the band in the cutouts provides a void space for the saw that avoids damage to the block, and the casting tape is severed and easily removed.

6 Claims, 2 Drawing Sheets

PROSTHETIC SOCKET ADJUSTABLE TEST MOUNTING SYSTEM

CROSS-REFERENCE TO RELATED APPLICATION(S)

The present invention derives priority from U.S. provisional application Ser. No. 61/206,893 filed 5 Feb. 2009.

BACKGROUND OF THE INVENTION

1. Field of the Invention

The present invention relates to prosthetics and, more particularly, to a prosthetic socket adjustable test mounting system to allow convenient testing and adjustment of post-operative prosthetic devices for above-the-knee and below-the-knee amputation patients.

2. Description of the Background

There are a variety of different types of prosthetic devices for patients that have had either transfemoral (above-knee) or transtibial (below the knee) amputation. A typical modern prosthesis device consists of a custom socket fitted over the residual limb, a structural component system affixed to the socket that may include a pylon and articulated replacement joints (such as a knee or ankle) depending on the patient and location of the amputation, and knee cuffs, belts or other systems to secure the device to the body. A prosthetic sock or liner is typically worn over the residual limb within the socket to cushion the area of contact, and, in some cases, realistic-looking skin is provided over the structural components for aesthetic reasons.

One of the primary concerns of prosthesis design and construction is that the device be lightweight and provide a comfortable fit to the residual limb, and a natural gait when in use. As such, many of its components are made of high strength plastics such as polypropylene which is commonly used for socket construction and considerable effort is expended shaping the socket to conform the wearer. Lightweight metals such as titanium and aluminum have replaced much of the steel in the structural components. Some of the newest prostheses use carbon fiber to form a lightweight pylon and other elements. Certain other parts of the limb (for example, the feet) have traditionally been made of wood (such as maple or poplar) and rubber although modern feet are more commonly constructed with a wooden inner keel under urethane foam. Other materials commonly used are plastics such as polyethylene, polypropylene, acrylics, and polyurethane.

To provide the user with a comfortable and natural gait, it is of primary concern that the prosthesis be properly aligned so that its movement conforms to the shape and movement mechanics of the wearer's body. For example, a prosthetic knee joint provides a pivoting motion between upper leg and lower leg components and the plane defined by the pivoting movement may have to be fixed at a particular angle with respect to the wearer's sagittal plane to maximize the comfort and ease of use of the prosthetic device. Similarly, in a prosthesis for a transfemoral amputee, the foot may have to be disposed at a suitable angle relative to the direction of travel and the leg prosthesis may have to conform to a wearer's adduction or abduction contracture angles if such are indicated. To facilitate assembly of the device that conforms to the wearer's needs, the components of the device must be held in proper alignment while they are interconnected. The primary alignment criteria are height of the socket from the knee joint, and of the knee joint to the foot, articulating angle of the knee joint, the relative angle of the upper leg components (socket) versus the lower leg components (transfemoral prosthetic limb), the degree of rotational freedom about the knee joint, and lateral displacement (or offset) of the upper leg component from the lower leg component. These primary alignment criteria are typically derived quantitatively by trial fitting and adjustment of a test prosthesis on the wearer, which is then used to collect anatomical references for use in making the finished prosthetic components. Once a test prosthesis has been fully fitted and adjusted a prosthetist will commonly employ a specialized alignment transfer jig for measuring the primary alignment criteria. More specifically, the steps involved in properly aligning the prosthetic are detailed as follows:

The first step in the prosthesis fabrication process is a dynamic fitting process by which the prosthetist evaluates the amputee and makes a casting or digital reading of the residual limb or stump. From the cast a positive model of the stump is formed as a basis for creating the socket. The prosthetist may modify the positive model by adding or removing material to account for the location of bones and tendons in the residual limb and enhance comfort in weight-bearing areas. Where a digital impression has been taken such modification may be made within the computer model. When the prosthetist is satisfied by the initial model a thermoplastic such as clear polycarbonate is vacuum-formed over the positive form to create a test socket. Use of thermoplastics allows for reheating and localized modification of the shape during the fitting process.

Clear diagnostic test sockets are used in order to allow the prosthetist to see contact and pressure points between the socket and stump during actual use and weight bearing conditions. Using the clear diagnostic test socket, the prosthetist assembles an entire diagnostic prosthesis and spends considerable time working with the patient to adjust and modify the relative position of the structural components to achieve the desired fit and alignment as described. The structural elements (knee, pylon, ankle, foot etc.) of the diagnostic prosthesis, which may or may not ultimately be those used in the definitive prosthetic device, are affixed to the diagnostic test socket via a test mounting block for test fitting and adjustment in order to determine the optimal alignment prior to construction of the definitive prosthesis. The test mounting block is a puck-shaped disc. Once the optimal alignment is achieved the test measurement are transcribed or an alignment duplicating device (transfer jig) is used to transfer the alignment to a definitive prosthesis.

During fitting, the test mounting block is bonded to the underside of the clear diagnostic socket using epoxy or other adhesive such as polyurethane, and the mounting block/diagnostic socket junction is wrapped with casting tape to reinforce the joint. After the alignment process is completed, the alignment data is recorded (or marked directly onto the test socket and tape), the now-hardened casting tape is cut-off, and the mounting block is removed as it is no longer needed. The tape is typically removed by sawing it off which, given conventional test mounting blocks, often damages the block and inevitably destroys the block. For this reason, prosthetists have traditionally improvised their own test mounting blocks by fashioning single-use wooden, or in some cases aluminum, devices. The scarring imparted by the sawing tends to render the mounting block damaged, deformed and unusable (even aluminum test mounting blocks after just a few uses). It takes considerable time and expense to fabricate each test mounting block, and it would be greatly advantageous to provide one capable of use, easy recycling, and reuse for as many test mountings as desired.

It is noteworthy that there are a variety of prior art mounting blocks, but all are for permanent attachment of a prosthetic socket to the structural components and cannot easily be removed without damage. Further, most mounting means of the prior art require multiple components (sandwich) to properly function and are thus considerably complex.

For example, U.S. Pat. No. 5,545,230 to Kinsinger, et al. discloses provides an interface block which is attached to the stump socket and includes a movable nut which extends from the interface block. The prosthesis can be attached to the movable nut utilizing a bolt, such that the position of the prosthesis is clamped in place when the bolt is tightened. The amputee can test the prosthesis to ensure it is properly oriented and/or positioned and adjust the alignment by loosening the bolt. Once a desired alignment is achieved a resin is injected into a cavity of the interface block to maintain the relative position. The block is thus incorporated into the definitive prosthesis and not for use and reuse in a diagnostic prosthesis.

U.S. Pat. No. 6,458,163 to Slemker et al. discloses a base block subassembly is attachable to a first prosthetic limb component and a coupling-socket adapter rotatably attached to the base block subassembly and having a cavity for receiving a male coupling member (such as a boss of a pyramidal link-block). Various mechanisms, including a ring having internal threads and a ring-clamp, are disclosed for locking the coupling-socket adapter against rotation with respect to the base block subassembly and for unlocking the coupling-socket adapter for rotation with respect to the base block subassembly, wherein the mechanisms are operable when the base block subassembly is attached to the first prosthetic limb component. The device is again for use in a definitive device.

U.S. Pat. No. 6,123,732 to Gramnas discloses an adjustable adapter for lower leg prostheses including an adapter housing attachable to the lower leg prosthesis, a spheroidal adapter head rotatable inside the housing and a prosthesis collar attachment member that can be shifted sideways relative to the adapter head, which member can be fastened to a prosthesis collar whereby the spheroidal part of the adapter head is on the exterior of the essentially tube shaped adapter head having an internally tube shaped part in which there are parts arranged to allow the prosthesis collar attachment member to be shifted sideways.

U.S. Pat. No. 6,051,026 to Biedermann, discloses an alignment device for connecting a stump socket to a prosthetic limb having an alignment member with an opening receiving a pin connected to the stump socket. The size of the opening is considerably greater than the cross-sectional dimension of the pin and the pin can be locked in any position within the opening.

U.S. Pat. No. 5,047,063 to Chen discloses an adjustment device for artificial limbs includes a hollow cylindrical member having an open upper section and an open bottom end, and a block member disposed on and covering the open bottom end. A coupling member is received in the hollow cylindrical member and has a top block portion to cover a central through opening of the block member, and a downwardly extending post portion projecting from the top block portion and having a diameter smaller than the central through opening. The post portion extends through the central through opening of the block member. The hollow cylindrical member is laterally movable to adjust the position of the post portion in the central through opening. The post portion extends into a sleeve member. A mounting member has a cylindrical portion with an upper surface which is provided with a concave recess. The sleeve member is tiltably received in the concave recess so as to guide the post portion in an inclined position relative to a vertical axis of the mounting member. The lateral position of the post portion in the through opening and the inclination of the post portion relative to the vertical axis of the mounting member is adjusted to correspondingly adjust the center of gravity of an artificial limb incorporating the adjustment device to match the body equilibrium of a user.

U.S. Pat. No. 5,163,965 to Rasmusson et al. discloses an attachment device for joining endoskeletal prosthesis to prosthetic sockets. The couplers provide a flat mounting block having an annular ring or notch on their side surfaces which define a void into which thermoplastic material can be molded to effectively secure the coupler to the definitive socket. A depression is provided in the top surface of the device to facilitate fitting to a prosthetic socket. No means for removal of the block are provided.

U.S. Pat. No. 6,669,736 to Slemker discloses substantially flat and strong distal attachment block or base for the deposition of the fused-deposition-modeling materials in order to incorporate the block into a socket in a CAD enabled rapid prosthetic manufacturing process. attachment block may have a notch machined or formed into its proximal surface, about a periphery thereof, for receiving a first layer of the solidifying material and providing at least two bonding surfaces for the solidifying material. No means of removing the block from the socket are provided.

U.S. Pat. No. 5,545,231 to Houser discloses A system for adjusting the angle between a pylon and prosthetic foot in either or both of the medial/lateral plane or the anterior/posterior plane by placing at least one wedge between the pylon and the prosthetic foot. A barrel nut mounted in the lower end of a prosthetic pylon mates with a bolt extending from the prosthetic foot to secure the foot to the pylon. The angle of the barrel nut is adjusted in the anterior/posterior plane so that a threaded bore of the barrel nut is aligned with the bolt as its angle varies according to the angle of the wedge positioned between the pylon and prosthetic foot.

None of the foregoing references facilitate the test mounting process, and so it would be greatly advantageous to develop a diagnostic socket alignment system including an improved mounting block that is reusable and that facilitates mounting of the structural components to the test socket in order to construct and align the diagnostic prosthesis as well as convenient recycling of all components.

SUMMARY OF THE INVENTION

Accordingly, it is an object of the present invention to provide a prosthetic component anchoring system which is easily and solidly attachable to a test socket constructed of thermoplastic or other material.

It is another object of the present invention to provide a prosthetic component mounting system to which the structural elements of the prosthesis may be easily and adjustably joined.

It is a further object of the present invention to provide a prosthetic component mounting system that can be removed without damage from the test socket of a diagnostic prosthesis after the alignment has been transferred so as to be reusable in subsequent diagnostic prostheses.

In accordance with an exemplary embodiment of the present invention, an adjustable temporary diagnostic prosthetic socket mounting system is provided in kit form comprising the components needed for a prosthetist to facilitate multiple test mountings of multiple test sockets. The kit includes a supply of casting tape, a supply of epoxy or other adhesive such as polyurethane, an indelible felt marking pen, a measuring tape, instructions, a recyclable test mounting block, and a plastic band or tape for encircling the test mounting block. The test mounting block has a closed form concave curvilinear perimeter shape (such as a circle) or concave parallelogram perimeter shape. The test mounting block is preferably constructed of aluminum or similar lightweight material the block has a diameter across its major axis in accordance with the distal end of the diagnostic socket (generally between 3-5 inches) and a thickness of approximately 20 mm (¾ inch) or as necessary to achieve a sufficiently rigid block. The perimeter of the block is defined by an annular groove within a range of from approximately 6-12 mm (¼-½ inch) deep. The annular groove is preferably formed with a "U" shaped cross sectional profile. Additionally, the perimeter of the block is defined by a plurality of axial grooves or cutouts (preferably 4) extending from the lower surface of the block to the upper surface. The axial grooves or cutouts may have shallow "U" shaped or other cross sectional profile and are as deep or preferably deeper than the annular groove. The plastic band is preferably a vinyl (or other plastic or rubber) pressure-adhesive material ring approximately 5-7 mils in thickness extending around the perimeter of the block. Alternatively, the kit may include a supply of pressure-adhesive vinyl or plastic tape such as electrical tape by which the prosthetist can fashion a band by wrapping around the perimeter of the block, and securing in place by pressure. The block is further defined by a center hole extending from the top surface to the bottom surface for maintaining vacuum within the diagnostic socket via a hole cooperatively drilled in the distal end of the socket, and a plurality of threaded mounting holes, preferably in a four hole European pattern, entering at least one surface of the block, and preferably passing through the block for screw-mounting a prosthetic limb thereto.

The included instructions define the method for use, by which the mounting block is secured to the clear diagnostic socket by an adhesive such as epoxy resin or, in some cases, by mechanical fasteners (such as screws). The vinyl band is then stretched and applied around the perimeter of the block over the annular groove, thereby establishing a clearance within the groove. Tension on the band or tape may cause it to deform into the annular groove somewhat while spanning the axial cutouts and it is important to establish a degree of clearance within the cutouts. Therefore, care should be taken to apply only enough tension to deform the band partially into the annular groove so as to ensure a gap is maintained between the band and the bottom of the axial cutouts. The band is wide enough to extend up over the upper edge of the block and onto the outer surface of the diagnostic socket. Casting tape is then applied over the socket/block joint (and over the band) to further secure it to the socket. A prosthetic limb is then attached to the underside of the mounting block. An optional adjustment plate may then be attached between the mounting block and limb. The adjustment plate is selectively adjustable in a plurality of planes including the horizontal plane so that the pitch and angle of the prosthetic limb can be altered to match the pitch and angle of the patient's natural leg while also allowing the entire limb to be translated in both the medial/lateral and anterior/posterior directions.

The prosthetist then applies the diagnostic fitting to the patient, and measures the fitting with the measuring tape provided for primary alignment criteria including height of the socket from the knee joint, and of the knee joint to the foot, articulating angle of the knee joint, the relative angle of the upper leg components (socket) versus the lower leg components (transfemoral prosthetic limb), the degree of rotational freedom about the knee joint, and lateral displacement (or offset) of the upper leg component from the lower leg component, and records the modifications necessary to produce a proper prosthesis. This may entail marking alignment marks directly on the diagnostic socket and or casting tape using the indelible felt pen provided.

On completion of the diagnostic fitting and recording of the alignment data, a cast saw or similar cutting tool can be passed around the perimeter of the block proximal to upper surface of the test block and between the block and the distal end of the diagnostic socket to cut the now hardened casting tape. The hardened adhesive filling the void space between the upper surface of the block and rounded distal end of the socket provides a sacrificial material and space in which the blade can pass without contacting and thereby damaging the block. The saw or cutting tool can then be passed vertically through the axial cutouts which have caused the casting tape to gap on application before hardening thereby again providing a void space in which to pass the blade. By this method the casting tape is severed into easily removed quadrants. The block can then be heated to release the remaining adhesive and the block gently pried away from the diagnostic socket without damage by inserting a tool into the center hole.

The above and other objects, features and advantages of the present invention will become readily apparent from the following detailed description thereof which is to be read in connection with the accompanying drawings.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention is a kit and assembly for securely but removably affixing the structural components of a prosthetic limb to a diagnostic socket for trial fitting and alignment. The kit comprises a supply of conventional prosthetic casting tape such as Delta-Lite™ Conformable Casting Tape or Delta-Lite Plus™. The kit also includes a supply of epoxy adhesive such as conventional modified epoxy acrylic resin or polyurethane resin as used in the prosthetic industry, an indelible felt marking pen, and a measuring tape. The kit further includes a recyclable test mounting block 10, a plastic band 16 or tape for encircling the test mounting block 10, and in some embodiments, a lateral/angular adjustment plate/mechanism.

Figure 1:
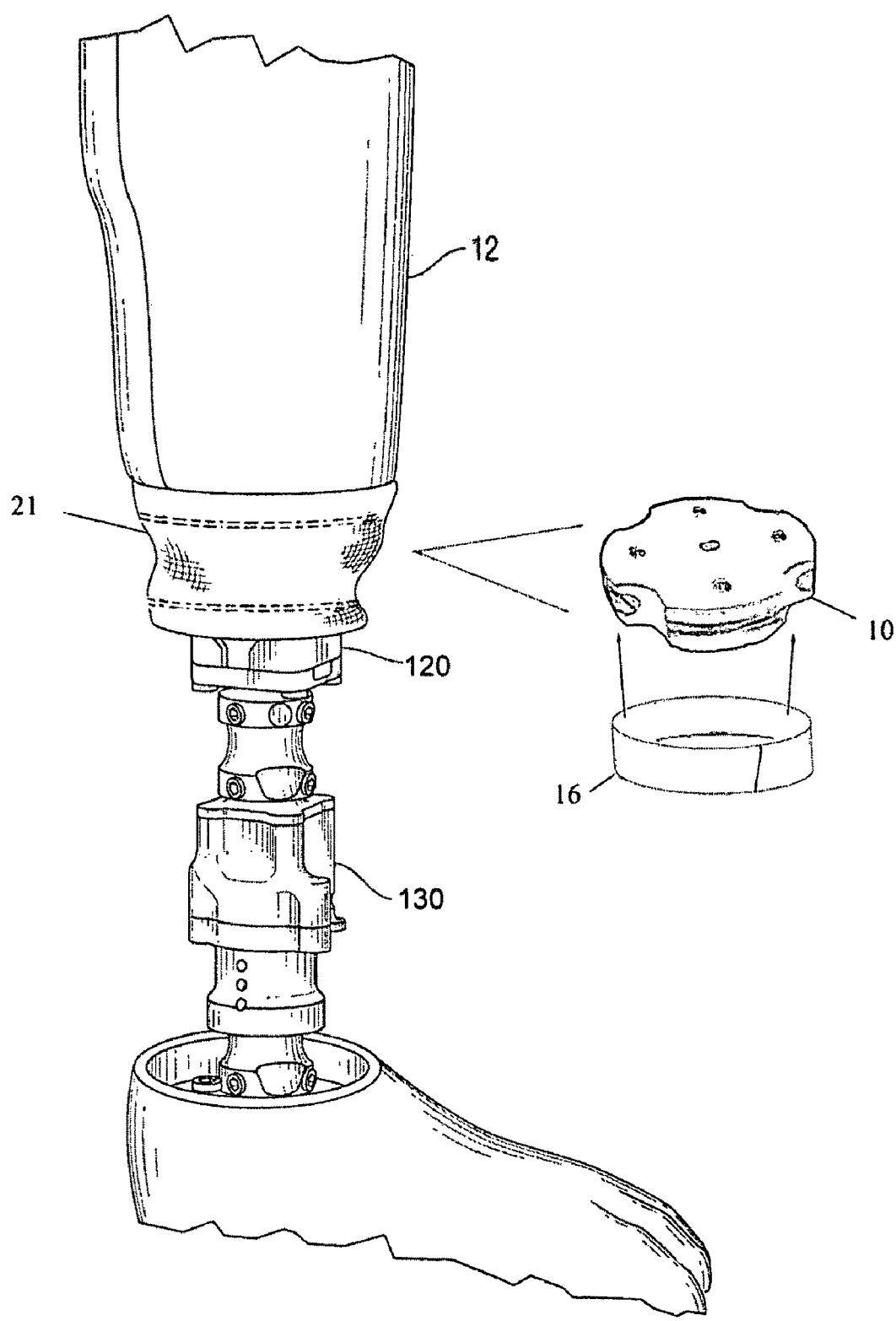
FIG. 1 is a perspective view of an exemplary diagnostic prosthetic in completed form with exploded breakout of the band and test mounting block according to the present invention.

FIG. 1 shows the mounting block 10 and plastic band 16 as would be incorporated in a completed diagnostic with exploded breakout of the band 16 and test mounting block 10 according to the present invention.

The block 10 has a closed-form disk shape with a broken peripheral groove 12, broken at each of a plurality of concave indents or recesses 13 into the disk. The overall disk shape is preferable circular, while the peripheral indents 13 are preferably rounded for safety but may be angular or squared. The block 10 is preferably constructed of aluminum or other durable material and has a diameter sized in accordance with the distal end of the diagnostic socket to be used (generally about 3-5 inches), and a thickness of approximately 20 mm (¾ inch) or as necessary to achieve a sufficiently rigid block of the selected material. In use the block 10 is adhered to the rounded distal end of the clear diagnostic test socket 12 using an epoxy, polyurethane or similar resin. After the prosthetist has adjusted the fit of the socket to his and the patient's satisfaction, taking advantage of the visibility provided by the clear diagnostic socket, a band 16 is applied around the block 10 and casting tape 21 is wrapped over the socket/block/band as shown to further secure it to the socket under test ambulation conditions. The prosthetic component(s) 130 may then be attached by its mounting flange 120 to the underside of the mounting block 10 or to an adjustment plate (not shown) affixed thereto.

Figure 2:
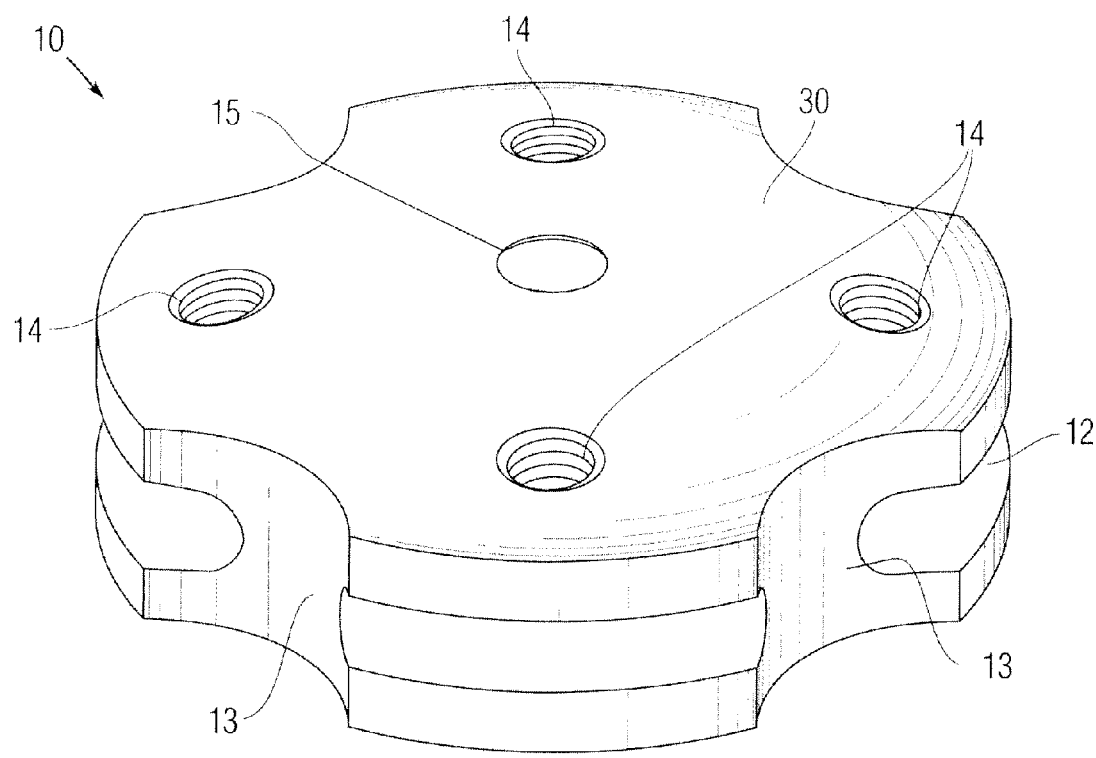
FIG. 2 is a perspective view of a mounting block according to the present invention.
Figure 3:
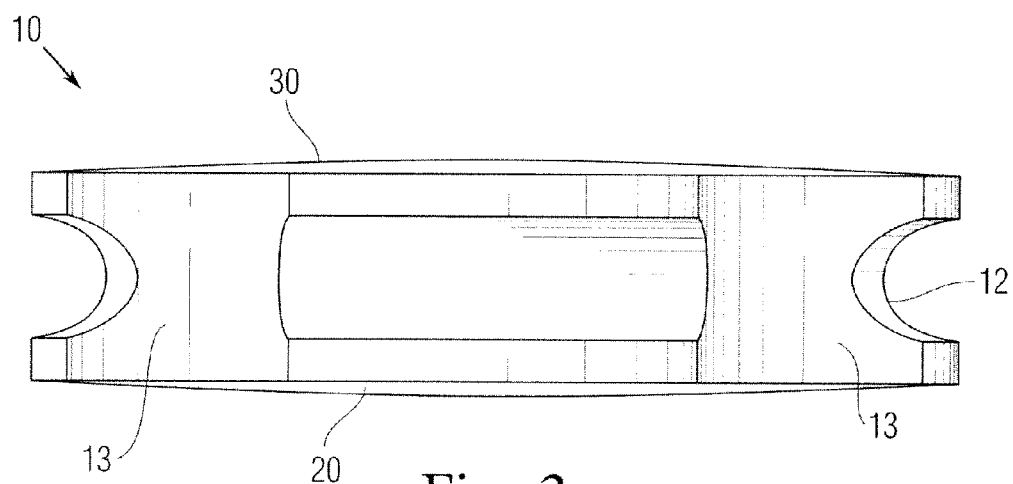
FIG. 3 is a side view of a mounting block according to the present invention.

FIGS. 2 and 3 are a perspective and side view, respectively, of the mounting block 10 as in FIG. 1. The perimeter of the block 10 is defined by the annular groove 12 which is approximately 6-12 mm (¼-½ inch) deep and substantially spanning approximately ⅔ the periphery of the block 10. The annular groove 12 is preferably formed with a "U" shaped cross sectional profile although other profiles such as a "V" notch or square notch may be utilized with only slightly diminished results as will be explained below. The perimeter of the of the block 10 is defined by, in a preferred embodiment, four axial recesses or cutouts 13 extending from the lower surface 20 of the block 10 to the upper surface 30. The axial recesses or cutouts 13 may have a wide, shallow "U" shape or again a "V" notch, square notch other cross sectional profile. Importantly, the axial grooves or cutouts 13 are as deep or, preferably, deeper than the annular grooves for optimal results. The block is further defined by a center hole 15 extending from the top surface 30 to the bottom surface 20 and a plurality of threaded mounting holes 14 on at least one surface of the block to which the prosthetic components may be secured. Mounting holes 14 are preferably in a four hole well-known European pattern, entering at least one surface of the block, and preferably passing through the block for screw-mounting a prosthetic limb thereto.

Referring back to FIG. 1, also provided as an element of the kit is an elastically and plastically deformable band 16. Vinyl of approximately 5-7 mils in thickness provides the desirable deformation properties although other plastics or other materials having similar deformation properties may be successfully utilized. The plastic band may be a pressure-adhesive tape formed in a continuous loop or may be a single strip wrapped around the perimeter of the block 10 and secured in place by adhesive or other means. Indeed the kit may include a supply of pressure-adhesive vinyl or plastic tape such as electrical tape by which the prosthetist can fashion a band by wrapping around the perimeter of the block, and securing in place by pressure.

In use the block 10 is secured to the diagnostic socket 35 by the supplied epoxy or urethane resin such as Fabtech Systems +PLUSeries™ 25-second two part structural urethane adhesive. The socket is then preliminarily fit to the patient's residual limb taking advantage of the transparency of the thermoplastic diagnostic socket. Once a satisfactory fit has been achieved the adhesive backed vinyl band 16 is tensioned and tightly applied around the perimeter of the block 10 at the annular groove 12. Tension on the band 16 causes it to deform into the annular groove 12 while spanning the axial cutouts 13, as depicted in FIG. 3. The band is wide enough to extend up over the upper edge of the block and onto the outer surface of the diagnostic socket. Care should be taken to apply only enough tension to deform the band partially into the annular groove 12 so as to leave a gap between the band 16 and the bottom of the axial cutouts 13 for subsequent removal. The casting tape 21 is then applied over the socket/block joint to further secure it to the socket. The applied tape 21 is wrapped around approximately the distal third of the socket extending over the block joint and into the groove 12 taking care not to apply the casting tape past the end of the applied band 16.

When the tape 21 has hardened the prosthetic components of the limb are attached to the underside of the mounting block 10 via holes 14. Where an electronically controlled vacuum system is be used the vacuum hose may be passed up into the socket via center hole 15. A translation device such as the 1K07-P.S.D.1 Translation Device for Trans-Femoral Prostheses by Proteor™ or similar sliding device (not shown) may be affixed to the block 10 to facilitate adjustment of the medial/lateral and anterior/posterior position of the components 130 in relation to the block 10 so as to achieve an optimum fit and alignment. If desired, an optional adjustment plate (also not shown) may be attached between the mounting block 10 and limb that is selectively adjustable in a plurality of planes so that the pitch and angle of the prosthetic limb can be altered in addition to the lateral position in order to match the pitch, angle and position of the patient's natural leg. Both the Proteor™ P.S.D., P.A.D. or other adjustment/adapter plate may be incorporated into the currently disclosed kit.

The prosthetist then applies the diagnostic fitting to the patient, and measures the fitting with the measuring tape provided for primary alignment criteria including height of the socket from the knee joint, and of the knee joint to the foot, articulating angle of the knee joint, the relative angle of the upper leg components (socket) versus the lower leg components (transfemoral prosthetic limb), the degree of rotational freedom about the knee joint, and lateral displacement (or offset) of the upper leg component from the lower leg component, and records the modifications necessary to produce a proper prosthesis. This may entail marking alignment marks directly on the diagnostic socket and or casting tape using the indelible felt pen provided.

On completion of the diagnostic fitting and transfer of the alignment, a cast saw or similar cutting tool can be passed around the perimeter of the block between upper surface 30 and the distal end of the diagnostic socket, cutting the casting tape and extending into the hardened urethane adhesive filling the gap between the rounded distal end of the socket and the flat upper surface 30 of the block 10. The saw or cutting tool can then be passed vertically through the axial cutouts 13 severing the casting tape into easily removed quadrants. Cutouts 13 provide a void through which the saw can pass without contacting or damaging the block 10. The void is maintained behind the casting tape 21 by the vinyl band 16. The quadrants of hardened casting tape 21 are easily pried away one section at a time with the band 16 acting as both a spacer and release surface to prevent the urethane resin or other hardening agent of the casting tape from adhering directly to the block 10. The block 10 can then be heated to release any epoxy or adhesive on the upper surface 30 and the block gently pried away from the diagnostic socket without damage by inserting a tool into the center hole 15.

In another alternate embodiment, square notch shaped axial cutouts 13 and angular groove 12 may be provided. In such a situation it may be beneficial to insert a soft foam band to partially fill the groove 12 or cutout 13 under (or in place of) the tape. The foam may be easily and sacrificially cut during later removal to ensure the saw does not contact and thereby damage the block 10.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A kit for temporarily securing components of a prosthetic limb to a diagnostic socket comprising:
    a block having a planar upper surface and a planar lower surface and a periphery there between, said periphery being defined by an annular groove, and a plurality of axial grooves extending from said upper surface to said lower surface, said axial grooves being at least as deep as said annular groove; and
    a band adapted to encircle the periphery of the block over the annular groove leaving a void space over said axial grooves.

2. The kit according to claim 1, wherein said band is a plastically deformable band of sufficient width to span said annular groove when applied to said periphery and extend onto an outer surface of said diagnostic test socket so as to partially deform into said annular groove while leaving a void space beneath said band within said axial groove.

3. A prosthetic socket adjustable test mounting kit, comprising:
    a block for temporarily securing components of a prosthetic limb to a diagnostic socket having a disk shape with a planar upper surface, a planar lower surface, and a side periphery, said side periphery being defined by an annular groove, and a plurality of recesses spaced about said periphery and interrupting said annular groove, said recesses being at least as deep as said annular groove; and
    a band adapted to encircle the side periphery of the block over the annular groove leaving a void space over each of said plurality of recesses.

4. The prosthetic socket adjustable test mounting block according to claim 3, wherein said disk has a closed form substantially circular shape.

5. The prosthetic socket adjustable test mounting block according to claim 4, wherein said plurality of recesses are arcuate concave.

6. The prosthetic socket adjustable test mounting block according to claim 5, wherein said plurality of recesses comprise four radially-spaced recesses.

* * * * *